(12) United States Patent
Faller et al.

(10) Patent No.: US 6,768,922 B2
(45) Date of Patent: Jul. 27, 2004

(54) DEFIBRILLATORS

(75) Inventors: Frederick W. Faller, Burlington, MA (US); Ward Hamilton, Amherst, NH (US)

(73) Assignee: ZOLL Medical Corporation, Chelmsford, MA (US)

(*) Notice: Subject to any disclaimer, the term of this patent is extended or adjusted under 35 U.S.C. 154(b) by 0 days.

(21) Appl. No.: 09/938,021

(22) Filed: Aug. 23, 2001

(65) Prior Publication Data

US 2003/0040775 A1 Feb. 27, 2003

(51) Int. Cl.⁷ ................................................ A61N 1/39
(52) U.S. Cl. ........................................................ 607/5
(58) Field of Search .................... 607/3, 4, 5; 206/438; D24/168

(56) References Cited

U.S. PATENT DOCUMENTS

| | | | |
|---|---|---|---|
| 3,804,082 A | * | 4/1974 | Tarjan et al. ................. 601/41 |
| 3,870,038 A | | 3/1975 | Arblaster ...................... 128/28 |
| 4,196,725 A | * | 4/1980 | Gunderson ............. 128/205.25 |
| 5,390,682 A | | 2/1995 | Iams .......................... 128/845 |
| 377,097 A | | 12/1996 | Olson et al. ............... D24/168 |
| 391,371 A | | 2/1998 | Coakley .................... D24/164 |
| 5,749,374 A | * | 5/1998 | Schneider, Sr. ............. 128/870 |
| 5,819,344 A | | 10/1998 | Otts .............................. 5/603 |
| 402,758 A | | 12/1998 | Barkley et al. ............ D24/167 |
| 6,149,670 A | * | 11/2000 | Worthen et al. ................ 607/3 |

* cited by examiner

Primary Examiner—Angela D. Sykes
Assistant Examiner—Roderick Bradford
(74) Attorney, Agent, or Firm—Fish & Richardson P.C.

(57) ABSTRACT

Defibrillators are provided that include a passive airway support device.

13 Claims, 9 Drawing Sheets

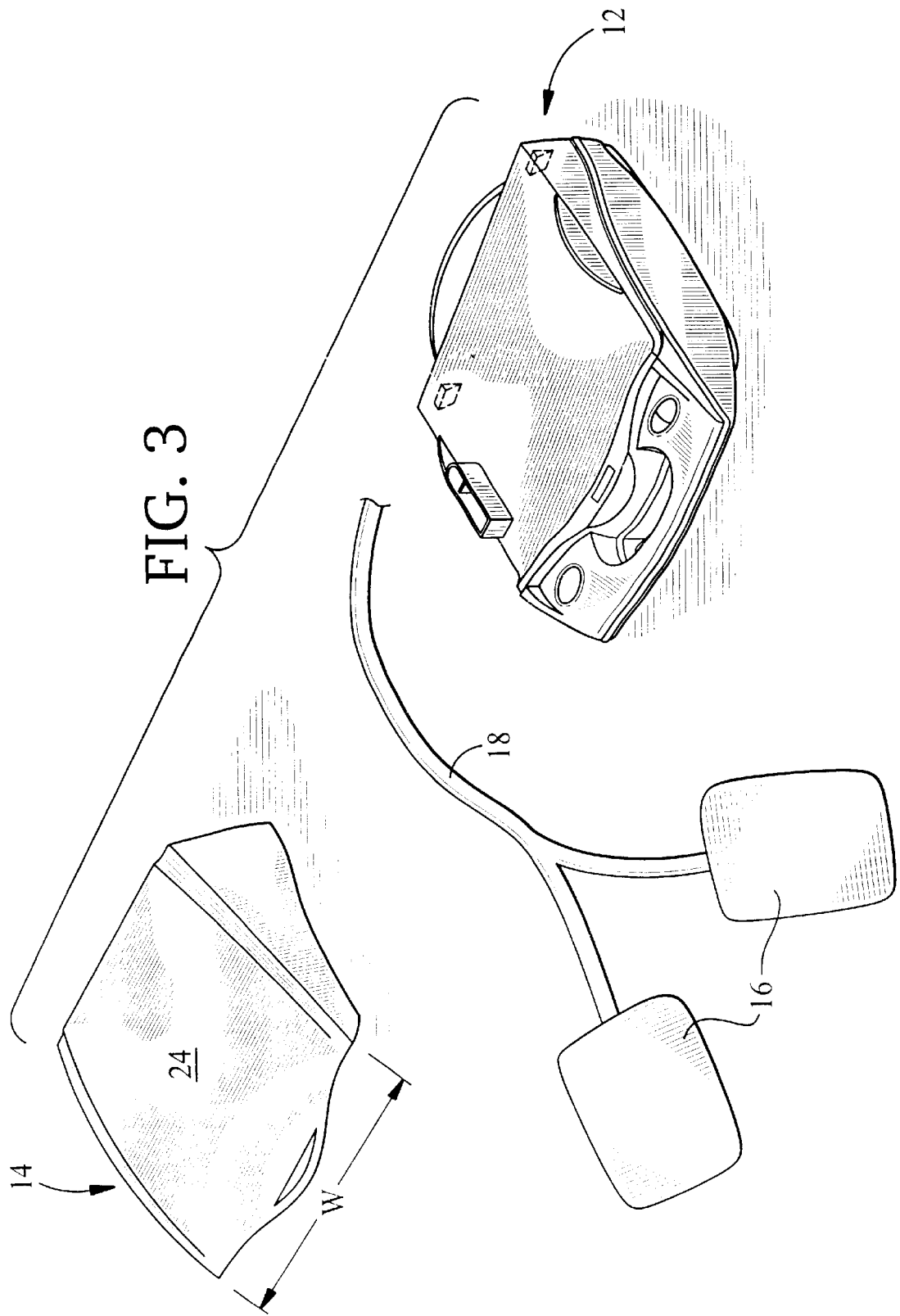

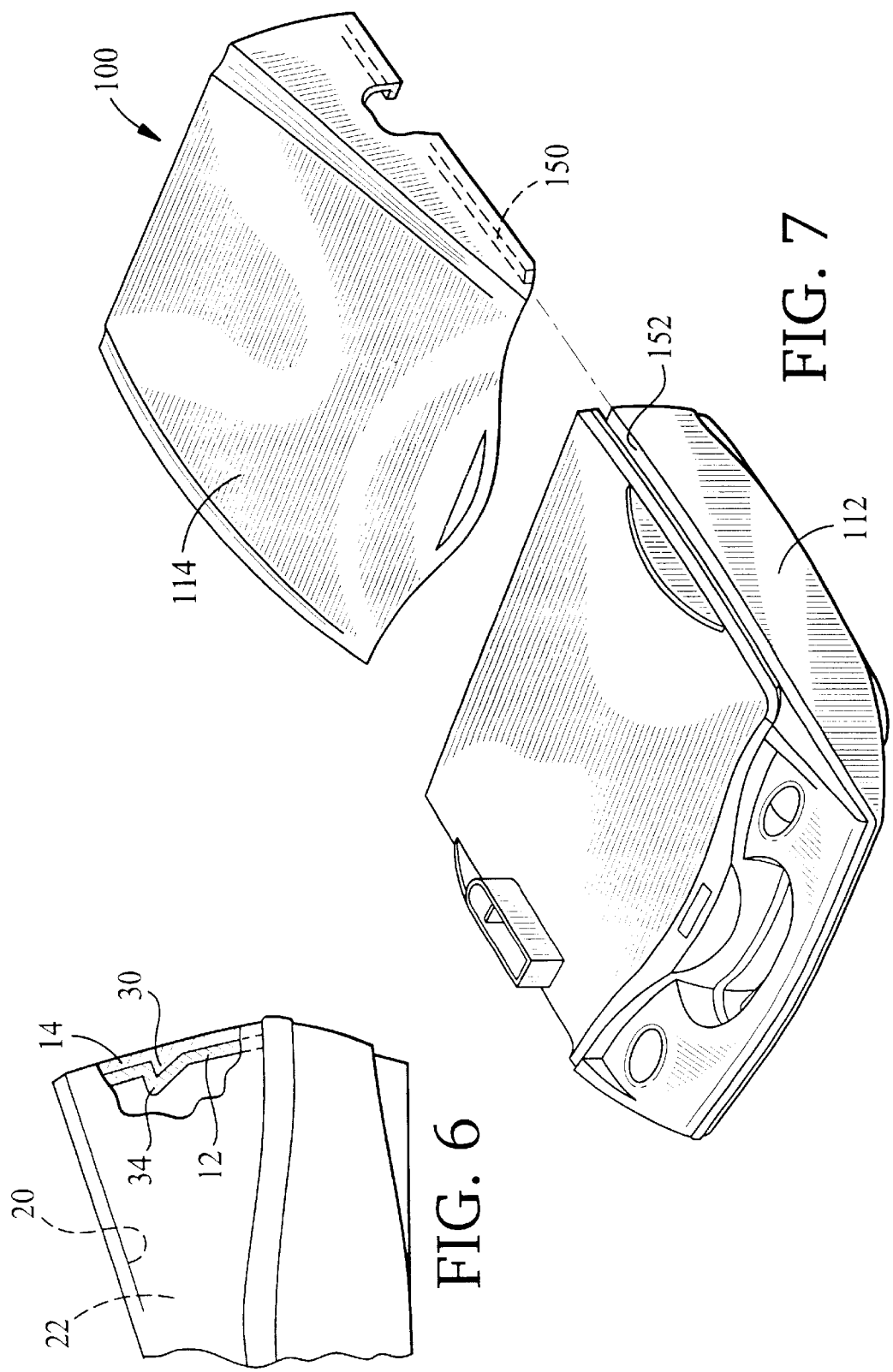

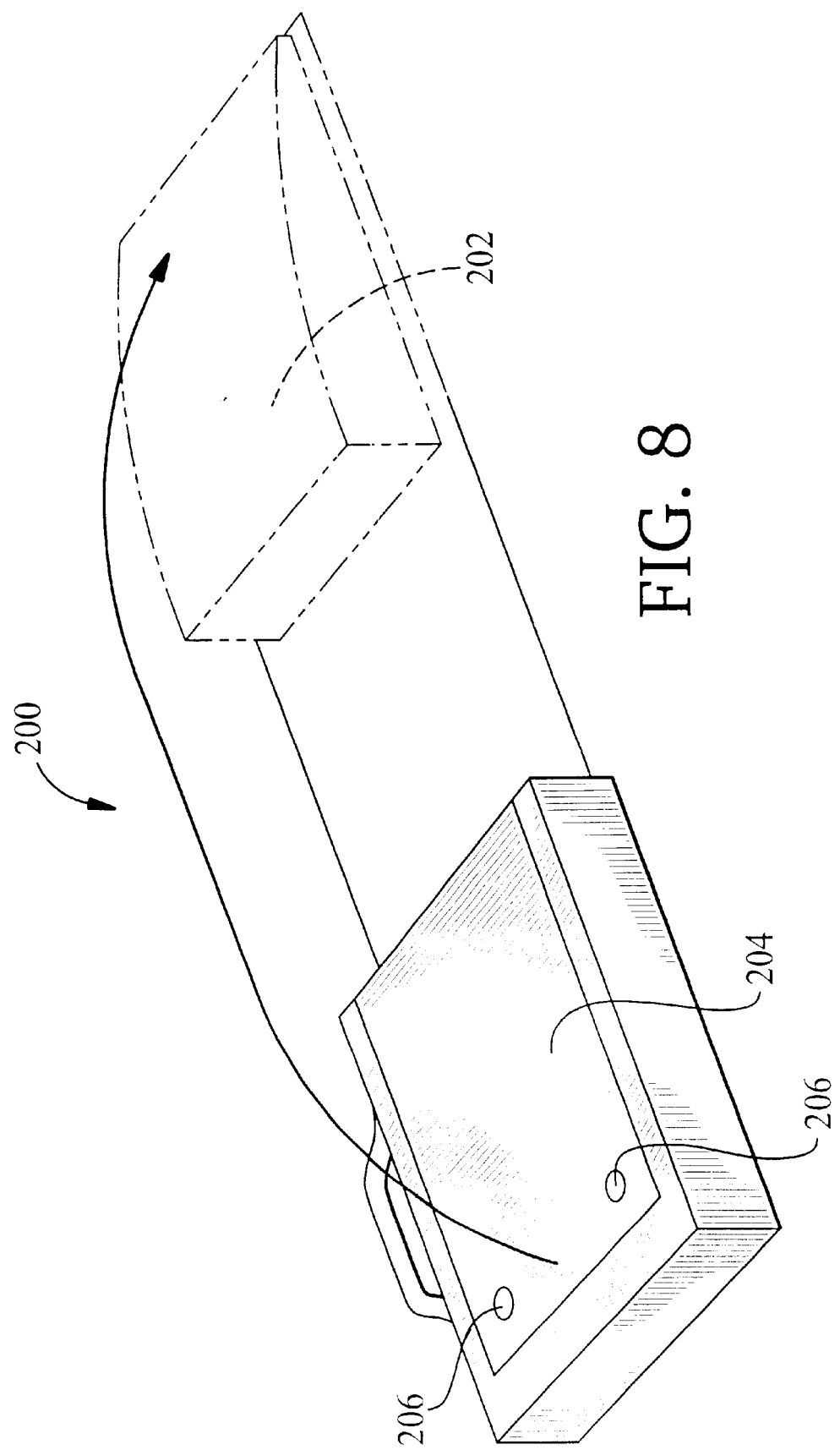

DEFIBRILLATORS

TECHNICAL FIELD

This invention relates to defibrillators.

BACKGROUND

Prior to administering treatment for cardiac arrest, the caregiver should make sure that the patient's airway is clear and unobstructed, to assure passage of air into the lungs. To prevent obstruction of the airway by the patient's tongue and epiglottis (e.g., as shown in FIG. 5), it is desirable that the patient be put in a position in which the neck is supported in an elevated position with the head tilted back and down. Positioning the patient in this manner is referred to in the American Heart Association Guidelines for Cardiopulmonary Resuscitation and Emergency Cardiovascular Care as the "head tilt-chin lift maneuver." The head tilt-chin lift position provides a relatively straight, open airway to the lungs through the mouth and trachea. However, it may be difficult to maintain the patient in this position during emergency treatment.

Resuscitation generally includes clearing the patient's airway, assisting the patient's breathing, performing chest compressions and defibrillation. Defibrillation can be performed using an automatic external defibrillator (AED). AEDs generally include a pair of electrodes connected to a resuscitation control box, which contains instrumentation for analyzing the patient's condition and providing a shock to the patient if appropriate.

SUMMARY

In one aspect, the invention features a defibrillator that includes a passive airway support device constructed to support a patient's shoulders and neck in a position suitable for maintaining airway patency and administering rescue breathing and resuscitation. Because the passive support device is included as part of the defibrillator, the passive airway support device will be readily available to the caregiver when needed. It is hoped that the availability of the device will lead to a high rate of usage by caregivers, potentially resulting in better airway maintenance and an improvement in the quality of care that is provided.

In one implementation, the passive support device is a removable portion of the resuscitation control box, for example a cover for the box.

Other features and advantages of the invention will be apparent from the detailed description and the drawings.

DESCRIPTION OF DRAWINGS

FIG. 3 is an exploded perspective view showing the defibrillator, electrodes and cover.

FIG. 6 is a partial cross-sectional view of the cover and defibrillator.

FIG. 7 is a perspective view of an automatic external defibrillator according to an alternate aspect of the invention.

FIG. 8 is a perspective view of an automatic external defibrillator according to another alternate aspect of the invention.

DETAILED DESCRIPTION

Figure 1:
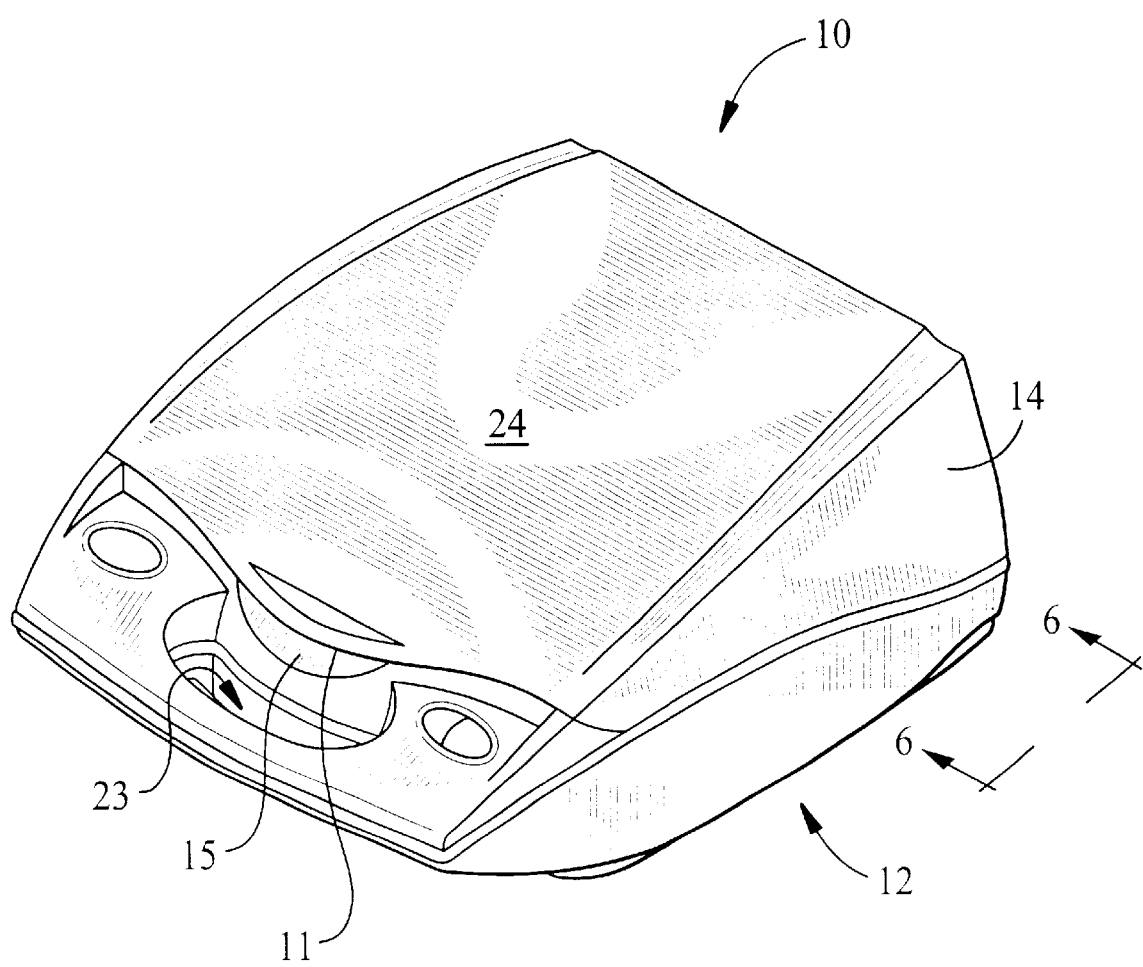
FIG. 1 is a perspective view of an automatic external defibrillator according to one aspect of the invention.
Figure 2:
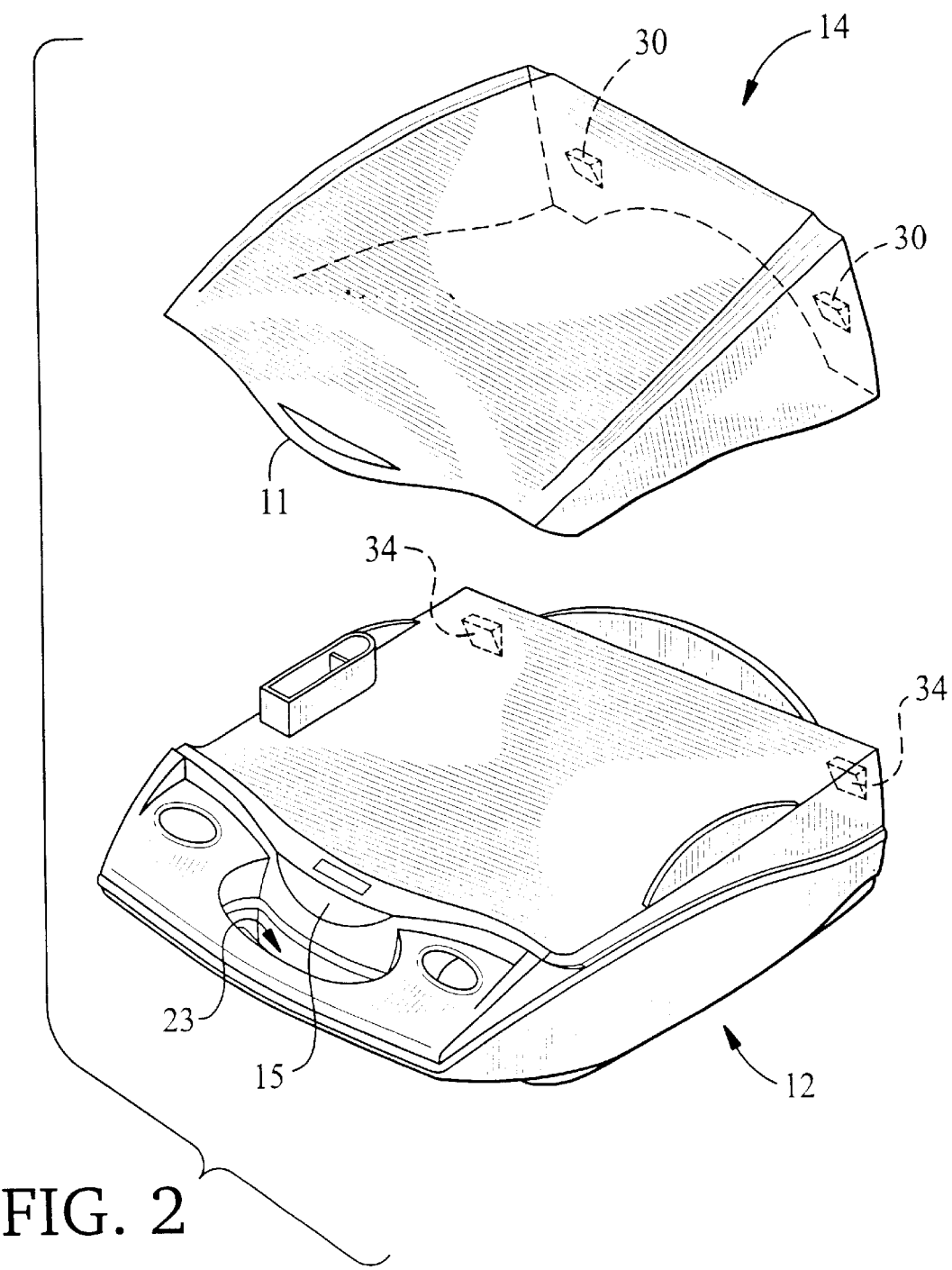
FIG. 2 is a perspective view of the automatic external defibrillator of FIG. 1 with the cover removed.
Figure 3A:
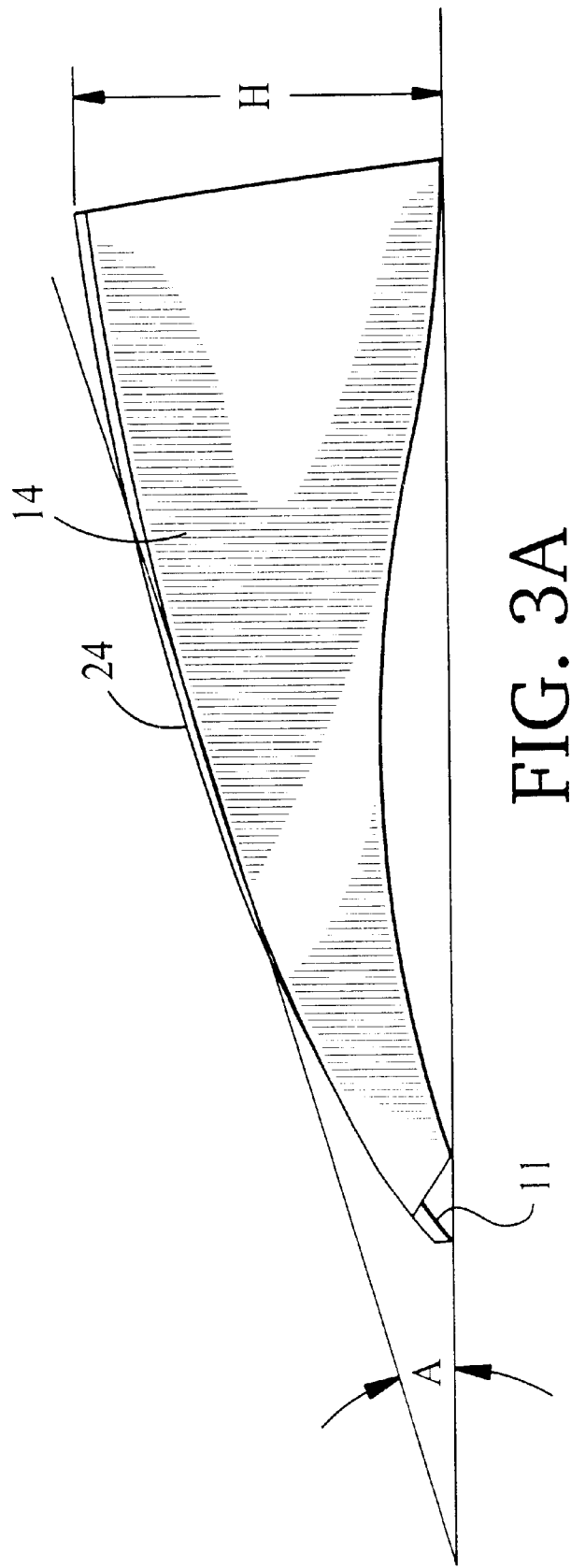
FIG. 3A is a side view of the cover.
Figure 3B:
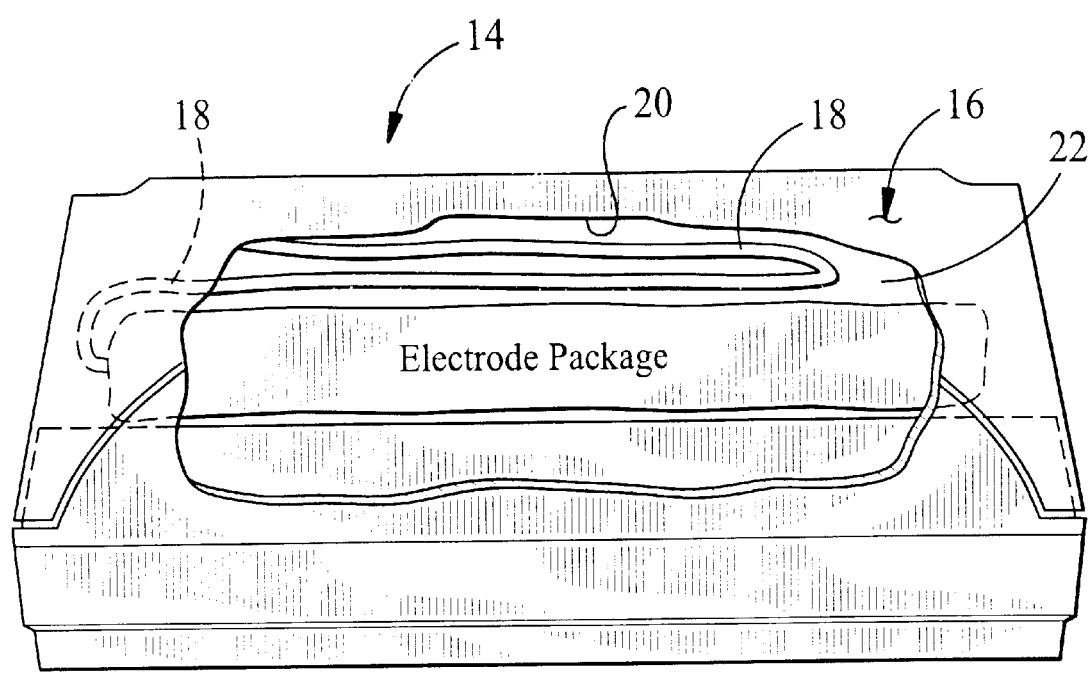
FIG. 3B is a back view of the automatic external defibrillator, with a portion of the cover cutaway to show the area between the cover and the top surface of the defibrillator box.

An automated external defibrillator 10 is shown in FIGS. 1 and 2. The defibrillator 10 includes a resuscitation control box 12 having a cover 14. A pair of electrodes 16 and a cable 18 connecting the electrodes to the box 12 are stored between the cover 14 and the control box 12. To accommodate the electrodes 16 and cable 18, the cover has a lower surface 20 that defines an open area 22 (FIG. 3B). The instrumentation of the defibrillator (not shown) is inside of box 12.

The cover press-fits onto the box 12. As shown in FIG. 6, protrusions 30 on cover 14, are constructed for releasable engagement with recesses 34 on box 12. The engagement of bumps 30 with recesses 34 holds the cover 14 in place until the cover 14 is removed by lifting it up and tilting it back, typically by inserting one's fingers into bevel 15 on control box 12 and thereby under lip 11 of the cover 14, and pushing up on lip 11.

Figure 4:
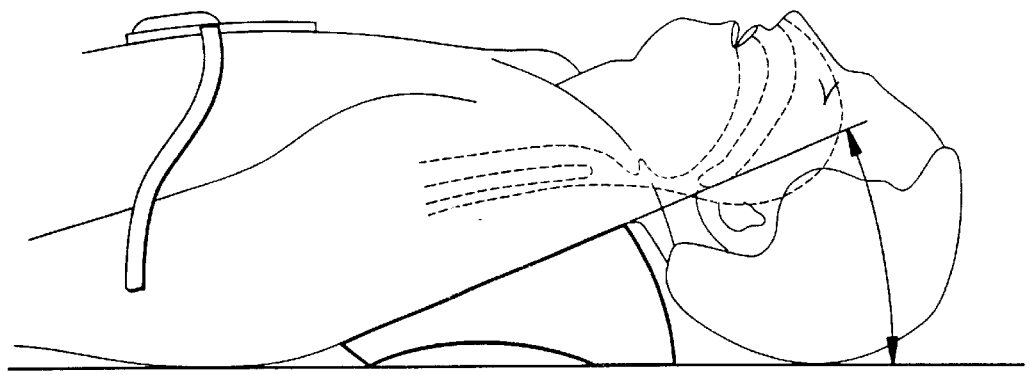
FIG. 4 is a side view showing the cover of FIG. 3 placed under a patient, with the airway indicated in phantom lines.

The cover is constructed to be positioned under a patient's neck and shoulders, as shown in FIG. 4, to support the patient's shoulders and neck in a way that helps to maintain his airway in an open position, i.e., maintaining the patient in the head tuck-chin lift position. The cover is preferably formed of a relatively rigid plastic with sufficient wall thickness to provide firm support during resuscitation. Suitable plastics include, for example, ABS, polypropylene, and ABS/polypropylene blends. Preferably, the cover has a wall thickness of from about 2.5 to 5.0 mm.

The cover 14 has an upper surface 24 that is inclined at an angle A (FIG. 3A) of from about 10 to 25 degrees, e.g., 15 to 20 degrees, so as to lift the patient's shoulders and thereby cause the patient's head to tilt back. The upper surface 24 is smoothly curved to facilitate positioning of the patient. A curved surface, e.g., having a radius of curvature of from about 20 to 30 inches, generally provides better positioning than a flat surface. At its highest point, the cover 14 has a height H (FIG. 3A) of from about 7.5 to 10 cm.

To accommodate the width of most patients' shoulders, the cover 14 preferably has a width W (FIG. 3) of at least 6 inches, e.g., from about 6 to 10 inches. If the cover 14 is not wide enough, the patient's neck and shoulders may move around during chest compressions, reducing the effectiveness of the device.

The edge of the cover may also include a lip 11 (FIG. 3A) or gasket (not shown) to prevent water from entering the box when the cover is in place.

When a caregiver encounters a person who appears to be suffering from cardiac arrest, the caregiver should follow recommended resuscitation procedures, such as are specified by the AHA Guidelines for Cardiopulmonary Resuscitation and Emergency Cardiovascular Care. If there is no evidence of head or neck trauma, the caregiver should clear any debris from the patient's airway. After this has been done, the caregiver should roll the patient onto his side, place cover 14 under the patient's shoulders, and roll the patient back onto his back. The cover should be positioned so as to support the patient in the position shown in FIG. 4, i.e., the head tilt-chin lift position. The caregiver can then proceed with CPR and/or use of the defibrillator.

Figure 5:
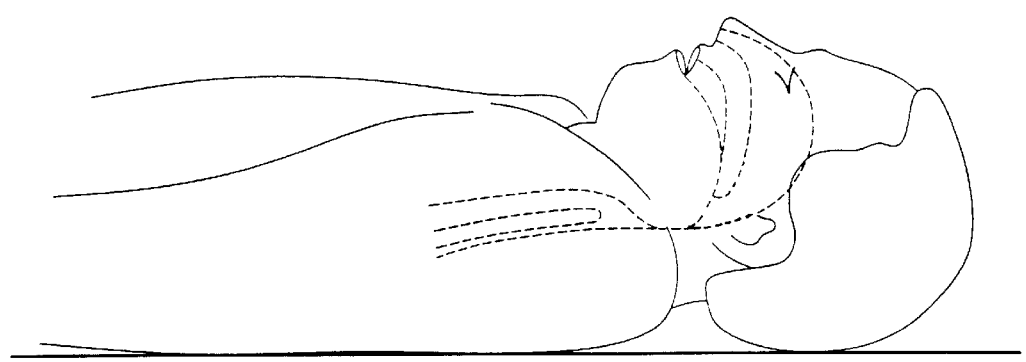
FIG. 5 shows the patient without the cover supporting the patient's neck and shoulders.

The positions shown in FIGS. 4 and 5 (a patient in the head lift-chin tilt position and a patient with a closed airway) are also shown in the AHA Guidelines for Cardiopulmonary Resuscitation and Emergency Cardiovascular Care, Aug. 22, 2000, p. 1–32, FIGS. 7 and 8.

Other embodiments are within the scope of the following claims.

For example, the passive airway support device may be used to assist patients who are not suffering from cardiac arrest, e.g., patients who are unresponsive but are breathing and have signs of circulation. For example, the device may be helpful in the treatment of patients who are suffering from suffocation and shock. The device is also useful for patients who are not breathing and are in need of rescue breathing, e.g., near-victims of drowning, and victims of respiratory arrest due to, for example, drug overdose, neurological problems, stroke, and smoke inhalation.

Moreover, the passive airway support device need not be the cover of the defibrillator, but may instead be some other portion of the resuscitator box, such as a base. The passive airway support device may be either removable or fixedly attached to the defibrillator box, provided that its use does not interfere with use of the defibrillator.

Rather than snapping onto the defibrillator box, the passive airway support device may slide onto the box. For example, in defibrillator 100, shown in FIG. 7, the passive airway support device is a cover 114 that includes rails 150 that slidably engage grooves 152 in box 112. The passsive airway support may, alternatively, be a base member that slides onto the box.

The passive airway support device may also be provided in the form of a briefcase or other carrier for the defibrillator, e.g., briefcase 200, shown schematically in FIG. 8. In this case, passive airway support device 202 is mounted on a flap 204 of semi-rigid material, e.g., plastic or stiff cloth. Flap 206 is releasably held in place by closures 206, e.g., snaps or hook and loop fasteners, allowing the flap to be easily detached and moved to the position shown in dotted lines in FIG. 8. When the flap is positioned in this manner, the briefcase 200 can be positioned under a patient and the support device 202 used in the manner described above.

Figure 9A:
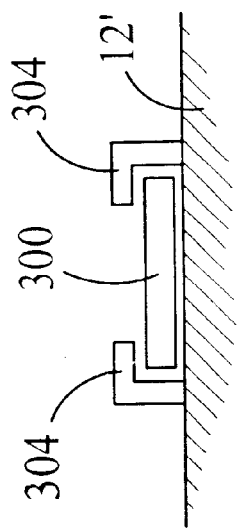
FIG. 9A is a highly enlarged partial top view showing the engagement of tabs 300 and members 304 in FIG. 9.
Figure 9:
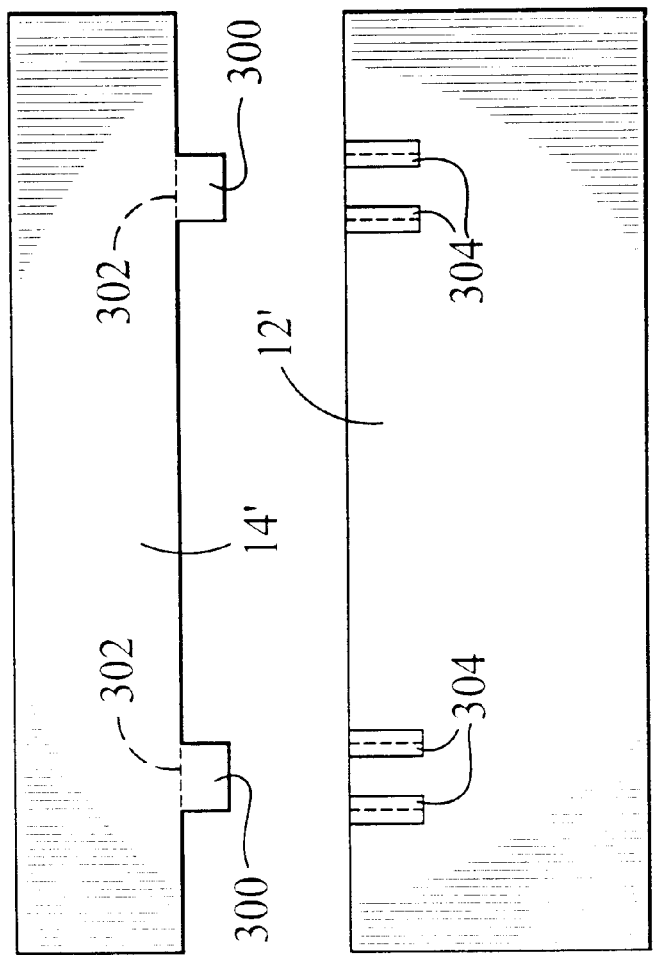
FIG. 9 is a diagrammatic exploded rear plan view of an automatic external defibrillator according to another alternate aspect of the invention.

If desired, the cover may be joined to the control box 12 by a releasable hinge, allowing the cover to be tilted back without the cover falling off of the box, but removed by either pulling straight up or tilting beyond a predetermined angle. For example, as shown in FIG. 9, the cover 14' may include a pair of tabs 300 joined to the cover by a living hinge 302. Each tab 300 slidingly engages a receptacle defined by a pair of opposed members 304 on control box 12' when the cover is in place. The cover can be tilted back, pivoting about the living hinge, or can be completely removed by pulling straight up and thereby releasing the sliding engagement of the tabs 300 in the slots 302. Alternatively, the cover may be joined to the control box by a separable hinge which disengages when the cover is tilted beyond a predetermined angle.

What is claimed is:

1. An external defibrillator comprising a housing;

defibrillator instrumentation disposed within the housing;

a pair of electrodes for being electrically connected to the instrumentation; and a cover removable from the housing, the cover serving both to cover a portion of the defibrillator when not removed from the housing and as a passive airway support device when removed from the housing, the passive airway support device being constructed to position and support a patient's neck and shoulders in a way that maintains the patient's airway in an open position during resuscitation, wherein the cover is configured so that the cover can be mechanically attached to the defibrillator prior to use of the defibrillator with the cover exposed on the exterior of the defibrillator prior to use, wherein the cover is configured so that it can be removed from the defibrillator when needed as an airway support, wherein the cover is formed from relative rigid plastic and is shaped to be placed under the shoulders and neck of the patient; and wherein the shape of the cover defines the shape of a portion of the defibrillator when the cover is not removed from the housing and defines the shape of the passive airway support when removed from the housing.

2. The external defibrillator of claim 1 wherein the cover includes a lower surface defining an open area between the cover and the housing dimensioned to receive the electrodes.

3. The external defibrillator of claim 2 wherein the cover has a wall thickness of from about 2.5 to 5.0 mm.

4. The external defibrillator of claim 1 wherein the passive airway support device includes an upper surface defining an angle A of from about 10 to 25 degrees.

5. The external defibrillator of claim 1 wherein the passive airway support device has a maximum height H of from about 7.5 to 10 cm.

6. The external defibrillator of claim 1 wherein the cover is constructed to removably press fit onto the housing.

7. The external defibrillator of claim 1 wherein the cover is constructed to slidably engage the housing.

8. The external defibrillator of claim 1 wherein the passive airway support device has a width of at least about 6 inches.

9. The defibrillator of claim 8 wherein the passive airway support device has a width of from about 6 to 10 inches.

10. The external defibrillator of claim 1 wherein the cover is mounted on the housing by a releasable hinge.

11. The external defibrillator of claim 10 wherein the releasable hinge comprises a protrusion on the cover or housing that is constructed to be releasably engageable with a recess or opening in an opposed portion of the housing or cover.

12. The external defibrillator of claim 1 wherein the cover has a curved surface.

13. The defibrillator of claim 1 wherein the cover has a wall thickness sufficiently thick to support the patient during resuscitation.

* * * * *